United States Patent
Schena et al.

(10) Patent No.: US 9,615,883 B2
(45) Date of Patent: Apr. 11, 2017

(54) SURGICAL PATIENT SIDE CART WITH SUSPENSION SYSTEM

(71) Applicant: INTUITIVE SURGICAL OPERATIONS, INC., Sunnyvale, CA (US)

(72) Inventors: Bruce Michael Schena, Menlo Park, CA (US); John Zabinski, Fremont, CA (US); David Robinson, Los Altos, CA (US); Paul G. Griffiths, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 14/276,996

(22) Filed: May 13, 2014

(65) Prior Publication Data
US 2014/0343570 A1    Nov. 20, 2014

Related U.S. Application Data

(60) Provisional application No. 61/823,626, filed on May 15, 2013.

(51) Int. Cl.
| | |
|---|---|
| *B62B 3/04* | (2006.01) |
| *A61B 19/00* | (2006.01) |
| *A61B 34/30* | (2016.01) |
| *A61B 50/13* | (2016.01) |
| *A61B 34/37* | (2016.01) |

(52) U.S. Cl.
CPC .......... *A61B 19/2203* (2013.01); *A61B 34/30* (2016.02); *A61B 34/37* (2016.02); *A61B 50/13* (2016.02)

(58) Field of Classification Search
CPC .................................. B60G 5/02; B60G 5/025
USPC ............ 280/47.34, 47.35, 47.41, 79.11, 79.2
See application file for complete search history.

(56) References Cited

U.S. PATENT DOCUMENTS

| | | | | |
|---|---|---|---|---|
| 2,805,079 | A * | 9/1957 | Vostrez | 280/79.11 |
| 2,931,156 | A * | 4/1960 | Fulwider | 56/320.1 |
| 2,978,255 | A | 4/1961 | Rosenkrands | |
| 3,154,164 | A * | 10/1964 | Shaw et al. | 180/209 |
| 3,534,978 | A * | 10/1970 | Stanfield | 280/79.2 |

(Continued)

FOREIGN PATENT DOCUMENTS

JP    2010008204 A    1/2010

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(Continued)

*Primary Examiner* — Jeffrey J Restifo
(74) *Attorney, Agent, or Firm* — Jones Robb, PLLC

(57) ABSTRACT

A patient side cart for a teleoperated surgical system comprises a base, a manipulator portion extending from the base and configured to hold one or more surgical instruments, four wheels mounted to the base to permit movement of the cart, and a suspension system. The suspension system may be configured to transition the cart between a first state in which the cart behaves as a three-wheeled cart and a second state in which the cart behaves as a four-wheeled cart.

30 Claims, 8 Drawing Sheets

(56) References Cited

U.S. PATENT DOCUMENTS

| | | | |
|---|---|---|---|
| 3,879,053 A * | 4/1975 | Chvala | 280/6.15 |
| 4,159,749 A * | 7/1979 | Boushek, Jr. | 180/308 |
| 4,512,589 A * | 4/1985 | Ambrose et al. | 280/5.502 |
| 4,647,067 A * | 3/1987 | Paquette et al. | 280/676 |
| 4,726,596 A * | 2/1988 | Ulmer | 280/33.994 |
| 5,639,119 A * | 6/1997 | Plate et al. | 280/754 |
| 5,871,218 A * | 2/1999 | Lepage et al. | 280/33.992 |
| 6,267,196 B1 | 7/2001 | Wilcox et al. | |
| 6,390,213 B1 * | 5/2002 | Bleicher | 180/65.1 |
| 6,394,216 B1 * | 5/2002 | Gordon | 180/311 |
| 6,796,568 B2 * | 9/2004 | Martis et al. | 280/124.111 |
| 7,090,042 B2 | 8/2006 | Coveyou et al. | |
| RE39,477 E * | 1/2007 | Nellers et al. | 280/754 |
| 7,273,115 B2 | 9/2007 | Kummer et al. | |
| 7,407,024 B2 | 8/2008 | Vogel et al. | |
| 7,416,188 B2 * | 8/2008 | Segerljung | 280/5.502 |
| 7,530,412 B2 | 5/2009 | Heimbrock et al. | |
| 7,533,892 B2 | 5/2009 | Schena et al. | |
| 7,661,493 B2 | 2/2010 | Rose | |
| 7,909,122 B2 | 3/2011 | Schena et al. | |
| 8,316,972 B2 | 11/2012 | Hutcheson et al. | |
| 8,419,030 B2 | 4/2013 | Lange et al. | |
| 2002/0093153 A1 * | 7/2002 | Scotese et al. | 280/6.153 |
| 2005/0257965 A1 * | 11/2005 | Segerljung | 180/41 |
| 2011/0127745 A1 | 6/2011 | Song et al. | |
| 2014/0343570 A1 * | 11/2014 | Schena et al. | 606/130 |

OTHER PUBLICATIONS

International Search Report and Written Opinion for Application No. PCT/US14/037913, mailed on Feb. 3, 2015, 14 pages.

* cited by examiner

SURGICAL PATIENT SIDE CART WITH SUSPENSION SYSTEM

This application claims the benefit of U.S. Provisional Application No. 61/823,626, filed on May 15, 2013, which is incorporated by reference herein in its entirety.

TECHNICAL FIELD

Aspects of the present disclosure relate to a suspension system for a mobile cart. In particular, aspects of the present disclosure relate to a suspension system for a teleoperated (robotic) surgical system patient side cart.

INTRODUCTION

Some minimally invasive surgical techniques are performed remotely through the use of teleoperated (robotically-controlled) surgical instruments. In teleoperated (robotically-controlled) surgical systems, surgeons manipulate input devices at a surgeon console, and those inputs are passed to a patient side cart that interfaces with one or more teleoperated surgical instruments. Based on the surgeon's inputs at the surgeon console, the one or more teleoperated surgical instruments are actuated at the patient side cart to operate on the patient, thereby creating a master-slave control relationship between the surgeon console and the surgical instrument(s) at the patient side cart.

A patient side cart may be located in a stationary position, such as during use of the patient side cart during surgery. On the other hand, a patient side cart need not remain stationary in a particular location but instead may be moved from one location to another. For example, a patient side cart may be moved from one location to another, such as from one location in an operating room to another location in the same operating room. In another example, a patient side cart may be moved from one operating room to another operating room, and even from one building to another building.

One consideration for a patient side cart, whether the patient side cart is stationary or being moved, is stability. For instance, it is desirable to ensure that a patient side cart does not lean or roll over during normal use, particularly for differing configurations of the cart and/or as the cart encounters irregular ground surfaces and/or obstacles in its path. Moreover, it is desirable that a cart has controlled drivability in differing configurations and/or as the cart encounters irregular ground surfaces and/or obstacles in its path.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a patient side cart for a teleoperated surgical system comprises a base, a manipulator portion extending from the base and configured to hold one or more surgical instruments, a first wheel and a second wheel, and oppositely extending arm portions that support the first wheel and the second wheel. The arm portions may be pivotable about an axis disposed between the arm portions.

In accordance with at least one exemplary embodiment, a patient side cart for a teleoperated surgical system comprises a base, a manipulator portion extending from the base and configured to hold one or more surgical instruments, a first pair of wheels, and a second pair of wheels. The first pair of wheels may be mounted to a first end portion of the base. The second pair of wheels may be mounted to the base via a suspension system disposed at a second end portion opposite the first end portion. The suspension system may be configured to permit relative movement of the base and the second pair of wheels toward and away from each other.

In accordance with at least one exemplary embodiment, a patient side cart for a teleoperated surgical system comprises a base, a manipulator portion extending from the base and configured to hold one or more surgical instruments, four wheels mounted to the base to permit movement of the cart, and a suspension system. The suspension system may be configured to transition the cart between a first state wherein a stability of the cart is that of a three-wheeled cart and a second state wherein the stability the cart is that of a four-wheeled cart.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
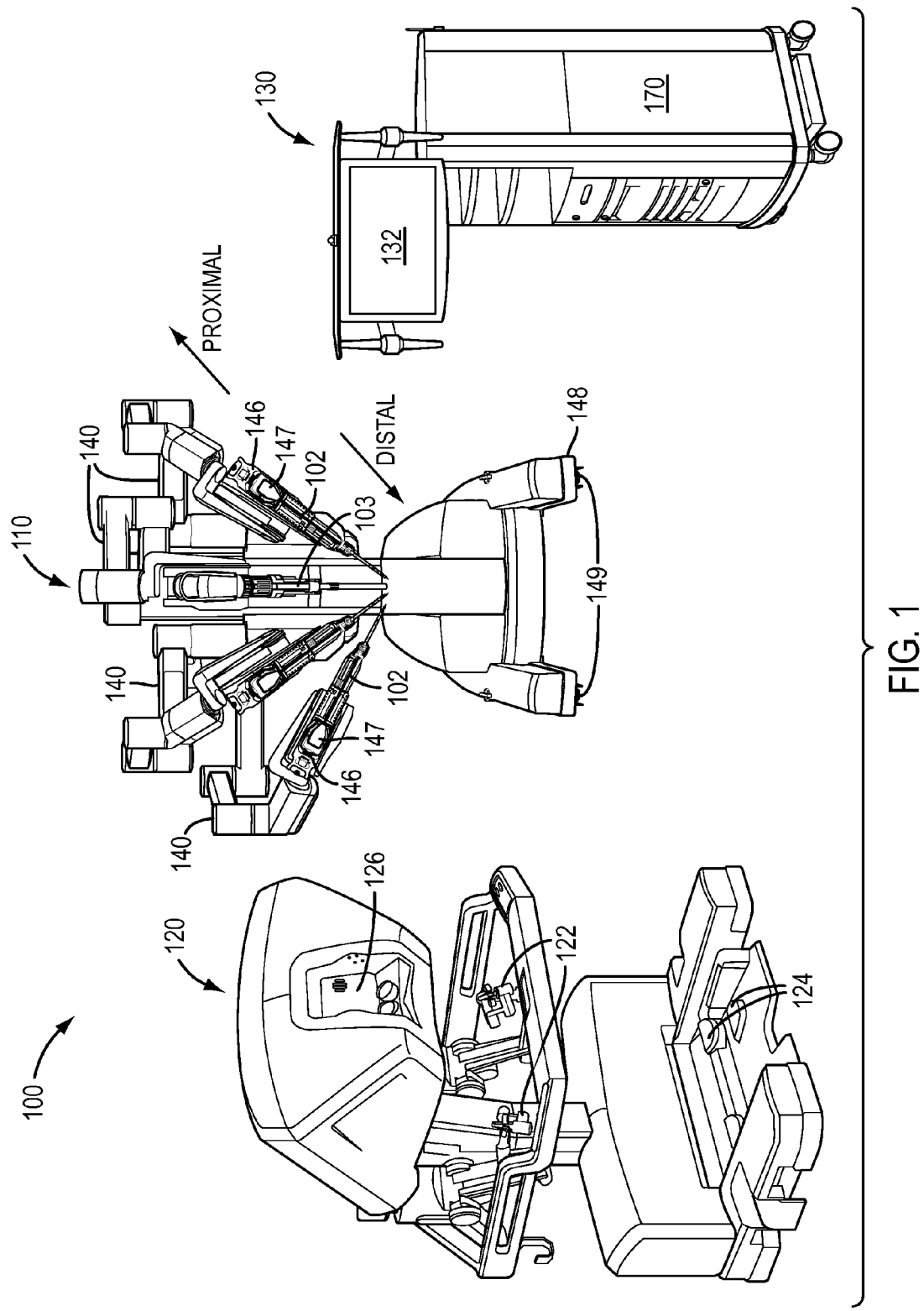
FIG. 1 is a diagrammatic view of an exemplary teleoperated surgical system in accordance with at least one exemplary embodiment.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Various exemplary embodiments of the present disclosure contemplate a cart with a suspension system that enables a cart having four wheels to behave like a cart having three wheels, in particular, in circumstances wherein a three-wheeled cart would be more stable than a four-wheeled cart. Such a cart may be, for example, a patient side cart of a teleoperated surgical system. Although various exemplary embodiments described below may refer to a patient side cart of a teleoperated surgical system, those having ordinary skill in the art would understand how to utilize the carts and suspension systems described herein for other wheeled platforms, such as, for example, imaging equipment, operating tables, and other wheeled devices.

The suspension systems in accordance with various exemplary embodiments can enhance the stability and control of a cart. The suspension system in various exemplary embodiments can permit the wheels of the cart to remain in contact with a ground surface by permitting a relative movement between a wheel and the cart. One or more wheels may be permitted to move in a substantially vertical direction toward or away from the cart. As a result, forces applied to the cart may be redistributed, such as when the cart is in an extreme deployed configuration, the cart traverses over a terrain with an irregular surface, or another external force is applied to the cart tending to unbalance (teeter) the cart. A suspension system in accordance with various exemplary embodiments may include an arm that pivots relative to the cart. The suspension system may further include two wheels, with a wheel mounted or otherwise attached to opposing portions of the arm. As a result, a cart with four wheels may act like a cart with three wheels due to the mounting of the pivotable suspension system to the cart. Thus, a cart may be stiff and stable when in a mode of behaving like a three-wheeled cart, such as on a flat or level ground surface or otherwise without external forces tending to teeter the cart, and may maintain traction between wheels and the ground surface. Additionally, the cart also can provide the stability of a four-wheeled cart, such as when the cart is on an irregular ground surface and/or other external forces are acting upon it that would tend to tip a three-wheeled cart over.

Further, although a cart in various exemplary embodiments may be a four-wheeled cart having a suspension system, the suspension system may not act like a suspension system for an automobile. For instance, the suspension system might not include compliant members that resist motion of a wheel throughout an entire range of motion of the wheel, as in an automotive suspension system.

With reference now to FIG. 1, a teleoperated surgical system 100 is provided which, in an exemplary embodiment, performs minimally invasive surgical procedures by interfacing with and controlling a variety of remotely operated surgical instruments, such as one or more surgical instruments 102, as those of ordinary skill in the art are generally familiar. The surgical instruments 102 may be selected from a variety of instruments that are configured to perform various surgical procedures, and in accordance with various exemplary embodiments can have a variety of configurations to implement surgical procedures of conventional surgical instruments. Nonlimiting examples of the surgical instruments 102 include, are but not limited to, instruments configured for suturing, stapling, grasping, applying electrosurgical energy, and a variety of other instruments with which those having ordinary skill in the art are generally familiar. A non-limiting, exemplary embodiment of a teleoperated surgical system with which the principles of the present disclosure may be utilized is a da Vinci® Si (model no. IS3000) commercialized by Intuitive Surgical, Inc. of Sunnyvale, Calif.

As illustrated in the schematic view of FIG. 1, the teleoperated surgical system 100 includes a patient side cart 110, a surgeon console 120, and a control cart 130. In non-limiting exemplary embodiments of the teleoperated surgical system, the control cart 130 includes "core" processing equipment, such as core processor 170, and/or other auxiliary processing equipment, which may be incorporated into or physically supported at the control cart 130. For instance, control cart 130 may also include a display 132 to provide an image, such as from an endoscope of patient side cart 110, and other controls for operating the teleoperated surgical system.

In general, the surgeon console 120 receives inputs from a user, e.g., a surgeon, using a viewer or display 126 and various input devices, including but not limited to, gripping mechanisms 122 and foot pedals 124, and serves as a master controller by which instruments mounted at the patient side cart 110 act as slaves to implement the desired motions of the surgical instrument(s) 102, and accordingly perform the desired surgical procedure. For example, while not being limited thereto, the gripping mechanisms 122 may act as "master" devices that may control the surgical instruments 102, which may act as the corresponding "slave" devices at the manipulator arms 140, and in particular control an end effector and/or wrist of the instrument as those having ordinary skill in the art are familiar with.

Based on the commands input to input devices at, for example, the surgeon console 120, the patient side cart 110 can position and actuate the instrument(s) 102 to perform a desired medical procedure via the actuation interface assemblies 146 at manipulator arms 140 of the cart 110. Manipulator arms 140 may each support an actuation interface assembly 146 and be configured to hold and manipulate various tools, including, but not limited to, for example, one or more surgical instruments 102 or an endoscope 103. The actuation interface assemblies 146 are configured to engage with transmission mechanisms 147 provided at a proximal end of the surgical instruments 102 (the general "proximal" and "distal" directions being shown in FIG. 1 relative to the surgical instrument). The surgical instrument 102 and the actuation interface assembly 146 may be mechanically and/or electrically connected to be able to operate the instrument 102.

To move a patient side cart from one location to another, a patient side cart is provided with one or more devices to provide movement to the cart. For example, the cart 110 can be provided with a plurality of wheels 149 attached to its base 148 to support and provide rolling motion to the cart 110, as shown in the exemplary embodiment of FIG. 1. In general, a patient side cart has a center of mass that can vary depending on the configuration of the cart (in particular the positioning of the patient side manipulator arms) and/or the terrain over which the cart is traversing when mobile.

Figure 2:
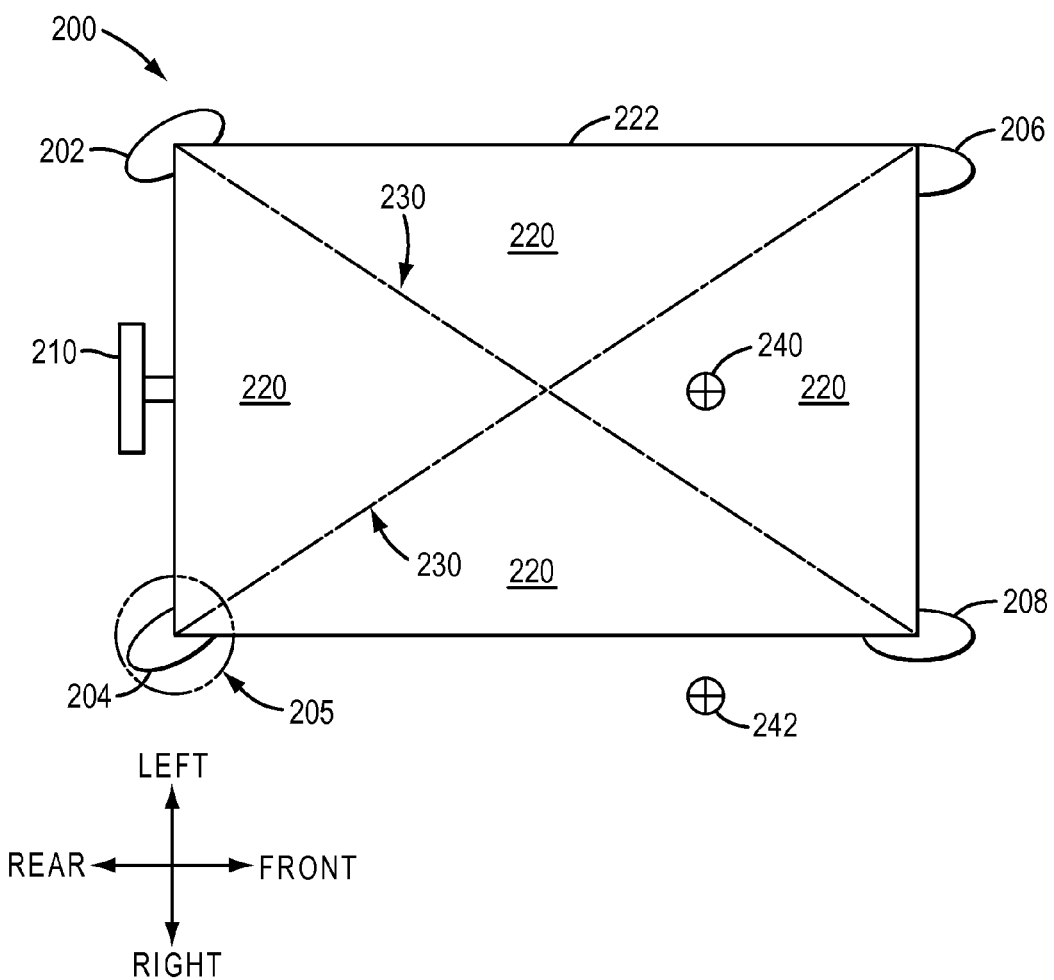
FIG. 2 is a schematic top view illustrating various stability zones of a conventional cart configuration based on a projection of a center of mass of the cart.

Turning to FIG. 2, a top view of a conventional patient side cart 200 is shown schematically with various illustrative aspects shown to illustrate principles associated with the present disclosure. The patient side cart 200 may have a configuration according to any of the exemplary embodiments described herein, such as with reference to FIG. 1 described above, and otherwise known to those having ordinary skill in the art. For example, a patient side cart 200 may include one or more surgical instrument(s) (not shown) and one or more patient side manipulator arms (not shown for simplicity) to which the surgical instrument(s) are coupled, as discussed above in regard to FIG. 1. Further, as shown in FIG. 2, a patient side cart 200 of a teleoperated surgical system may include a steering interface 210 that receives input from a user indicating what direction the user would like the patient side cart 200 to move in.

A patient side cart 200 also may include wheels on the underside of its base to permit movement of the cart. The wheels of the patient side cart 200 have a conventional configuration and are vertically static, i.e., fixed to a bottom portion of the cart 200. For example, a patient side cart 200 may include four wheels 202, 204, 206, 208, as shown in FIG. 2. Wheel 202 may serve as a left rear wheel, wheel 204 may serve as a right rear wheel 204, wheel 206 may serve as a left front wheel, and wheel 208 may serve as a right front wheel in relation to the left, right, front, and rear directions indicated in FIG. 2. Another configuration of a patient side cart may have three wheels instead of four. For instance, a patient side cart 200 may include two front wheels 206, 208 and a single rear wheel (not shown) in a central portion of the rear of the cart that would be provided in lieu of wheels 202 and 204. Those of ordinary skill in the art are familiar with various three-wheeled cart configurations. One or more of the wheels 202, 204, 206, 208 of a patient side cart 200 of FIG. 2 may be driven by a drive system included in the patient side cart 200 that provides motive force to the driven wheel(s).

One or more wheels of a patient side cart may be free to rotate about a vertical axis. For instance, rear wheels 202, 204 of patient side cart 200 in FIG. 2 may be free to rotate about a vertical axis extending into and out of (e.g., substantially perpendicular to) the page of FIG. 2. According to an exemplary embodiment, wheels that are free to rotate about such a vertical axis are not driven by a drive system of a patient side cart. For instance, rear wheels 202, 204 may be caster wheels that are not driven by a drive system of patient side cart 200. Because rear wheels 202, 204 may be free to rotate about a vertical axis, the location of the contact area between a wheel and a ground surface may vary as the wheel rotates. For instance, using wheel 204 in FIG. 2 as an example, as wheel 204 rotates about a vertical axis, the contact area between wheel 204 and a ground surface may sweep through an area 205.

A patient side cart may be located in a stationary position, such as during use of the patient side cart during surgery, or a patient side cart may be moved from one location to another. For example, a patient side cart may be moved from one location to another, such as from one location in an operating room to another location in the same operating room. In another example, a patient side cart may be moved from one operating room to another operating room, or even from one building to another building. Movement of a patient side cart may result in some degree of instability for the cart. Instability also may be caused by the configuration of the patient side cart, such as how manipulator arms are extended. Instability may manifest as motion of manipulator arms and/or a loss of traction between one or more wheels and a ground surface. For instance, instability may result in one or more wheels of the patient side cart to be lifted upward so that the one or more wheels no longer engage a ground surface. If the wheel(s) lifted from the ground surface are driven to move a patient side cart, it may become difficult to move the cart in a desired manner. Therefore, it may be desirable to provide a cart with enhanced weight distribution and balance to address these issues.

The behavior of an object like a four-wheeled cart may depend upon the type of ground surface the cart is located upon. To demonstrate this behavior, a center of mass of a patient side cart 200 may be projected onto the view shown in the exemplary embodiment of FIG. 2. Generally speaking, rectangle 222 represents a boundary in which a stable zone 220 is located, although the shapes and locations of rectangle 222 and stable zones 220 may vary and are not limited to the exemplary embodiment shown in FIG. 2. When the cart is located upon a flat, level ground surface, all four wheels 202, 204, 206, 208 of cart 200 are in contact with the ground surface at a given time. In such a state, cart 200 will not topple over and may be considered to be stable. As an example, a center of mass may be located at position 240 in stable zone 220 within rectangle 222 in this state. Conversely, should a center of mass project outside of rectangle 222, such as at position 242, cart 200 is unstable and will tip over.

Figure 3:
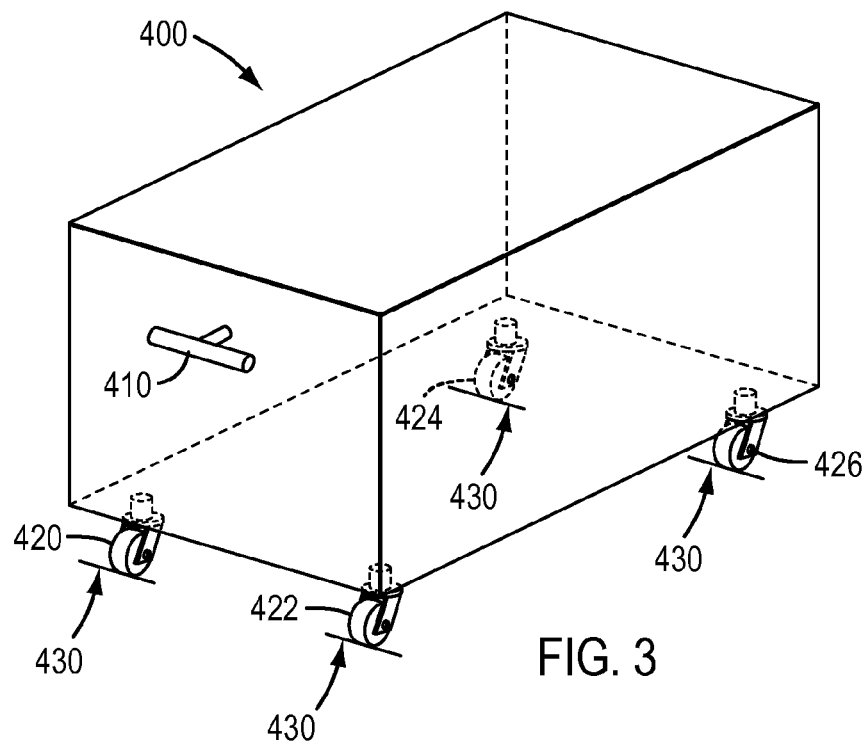
FIG. 3 is a schematic perspective view of an exemplary embodiment of a cart traversing a level ground surface to illustrate aspects of the present disclosure.

Further, if a ground surface is flat and all four wheels 202, 204, 206, 208 are in contact with the ground surface, cart 200 has traction with the ground surface for all of the wheels. Such a state is depicted in the exemplary embodiment of FIG. 3, in which a patient side cart 400 is on a substantially level ground surface 430 with wheels 420, 422, 424, 426 in contact with ground surface 430. Patient side cart 400 may include a steering interface 410 and may include the features of the patient side cart 110 shown in the exemplary embodiment of FIG. 1, some of the features of which, such as manipulator arm(s) and surgical instrument(s), are not shown in FIG. 3 for ease of viewing.

Figure 4:
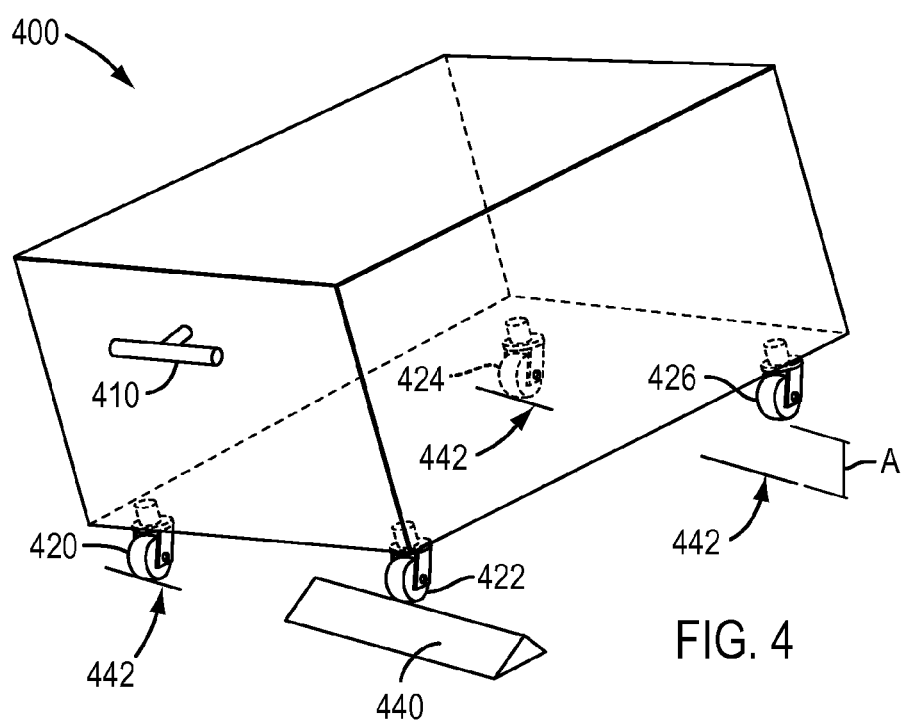
FIG. 4 is a perspective view of an exemplary embodiment of a patient side cart traversing over a protuberance on a ground surface.

In contrast, when a ground surface is irregular (i.e., a ground surface has protuberances and/or recesses), one wheel of a cart may lose contact with the ground surface. Turning to FIG. 4, an exemplary embodiment of a patient side cart 400 is shown on an irregular ground surface 442, for example a ground surface 442 that includes, for example, a localized protuberance 440. Protuberance 440 could result, for example, from a ground surface 442 that has generally rough terrain, from a localized topology of the ground surface (e.g., a bump or divot), and/or from objects placed on a ground surface, such as a cable or other object that might be found on the floor of an operating room, for example. Although a protuberance 440 is shown in the exemplary embodiment of FIG. 4, a recess (not shown) could be provided instead, which would provide a similar effect because a wheel located within the recess would lose contact and traction with a ground surface.

When the cart 400 moves over the irregular ground surface 442 and a wheel of the cart 400 engages the protuberance 440, such as right rear wheel 422, one wheel may be lifted upward from contact with the ground surface 442. For instance, right front wheel 422 may be lifted off of ground surface 442 by a distance A, as shown in FIG. 4. If right front wheel 426 is driven, the movement of the cart 400 may be affected because right front wheel 426 no longer has traction with the ground surface 442. Furthermore, if a cart 400 is steered in a desired direction by driving wheels at different speeds, such as by driving left front wheel 424 and right front wheel 426 at different speeds, irregular ground 442 may affect the steering of the cart 400 since one of the front wheels 424, 426 could be lifted off of ground surface 442. Thus, although cart 400 may be considered stable, the loss of traction may affect the driving and steering of cart 400.

When a cart is on an irregular ground surface and one wheel loses contact with the ground surface, the cart may be in a state of teetering. Teetering behavior may be demonstrated, for example, by drawing a "teeter axis" 230 between the areas of contact between a ground surface and wheels 202, 208, as shown in FIG. 2. In such a state, wheels 202, 208 are in contact with the ground surface but cart 200 may be rocked about axis 230, with either wheel 204 in contact with the ground surface and wheel 206 not in contact with the ground surface, or wheel 206 in contact with the ground surface and wheel 204 not in contact with the ground surface. For instance, if a center of mass (not shown) is located upon "teeter axis" 230 extending between wheels 202, 208, a force may shift the center of mass to either side of the "teeter axis" 230. Thus, a force may shift the center of mass towards wheel 204, causing wheel 204 to contact the ground surface while wheel 206 is not in contact with ground surface, or a force may shift the center of mass towards wheel 206, causing wheel 206 to contact the ground surface while wheel 204 is not in contact with ground surface. A "teeter axis" 230 may also be drawn between the areas of contact between a ground surface and wheels 204, 206, which may result in similar behavior with wheels 204, 206 maintaining contact with the ground surface and wheels 202, 208 alternating in contact with the ground surface, as described above for wheels 204, 206 when a "teeter axis" 230 is drawn between the contact regions for wheels 202, 208.

Those having ordinary skill in the art would appreciate that the shape and/or location of teeter axes 230 of cart 200 are not limited to what is shown in the exemplary embodiment of FIG. 2. For instance, the location of teeter axes 230 will depend both on the positioning of cart wheels 202, 204, 206, 208 (e.g., if a wheel is permitted to turn about a vertical axis, such as a caster wheel 204 through a contact area 205, the position of the line between ground contact points of diagonally opposite wheels (i.e., the teeter axis) may shift position as well) and the unevenness of the ground on which the wheels are resting. Further, although teeter is described above with regard to a cart on an irregular ground surface, teetering may also occur due to irregularities with the wheels of a cart. For instance, one or more wheels of a cart may have a contact surface, such as a bottom surface of a wheel, which is at a different vertical height than other wheels, which may result in teetering behavior.

As described above with regard to the exemplary embodiment of FIG. 2, when teetering occurs one wheel loses contact with a ground surface. As a result, the wheel can lose traction, which may affect the driving and/or steering of a cart in a desired manner, as described above in regard to the exemplary embodiment of FIG. 4. Further, when a cart teeters, the cart itself moves, which may result in movement of components of the cart, such as the manipulator arms.

Other factors may affect the behavior of a cart (e.g., patient side cart 110 (FIG. 1)) aside from the ground surface over which the cart is traversing. According to an exemplary embodiment, the configuration of the cart may affect the behavior of the cart. Because a patient side cart (such as patient side cart 110) may include movable components to perform surgery, as commanded by a surgeon, such as one or more manipulator arms 140 (FIG. 1), with or without one or more surgical instruments 102 (FIG. 1) mounted thereto, the movement and disposition of such components and their respective masses may shift the center of mass of the patient side cart 110. The manipulator arms 140 and their respective instruments and other components may be folded in a relatively compact arrangement, or the manipulator arms may be extended, such as to one side of the cart, causing a shift in the center of mass (e.g., the center of mass indicated at position 240 in FIG. 2) of the cart 110. Such a shift in the center of mass could cause movement of the manipulator arms 140 and their respective instruments and other components, particularly when the cart 110 is teetering from one wheel to another, as discussed above with regard to the exemplary embodiment of FIG. 2.

Figure 5:
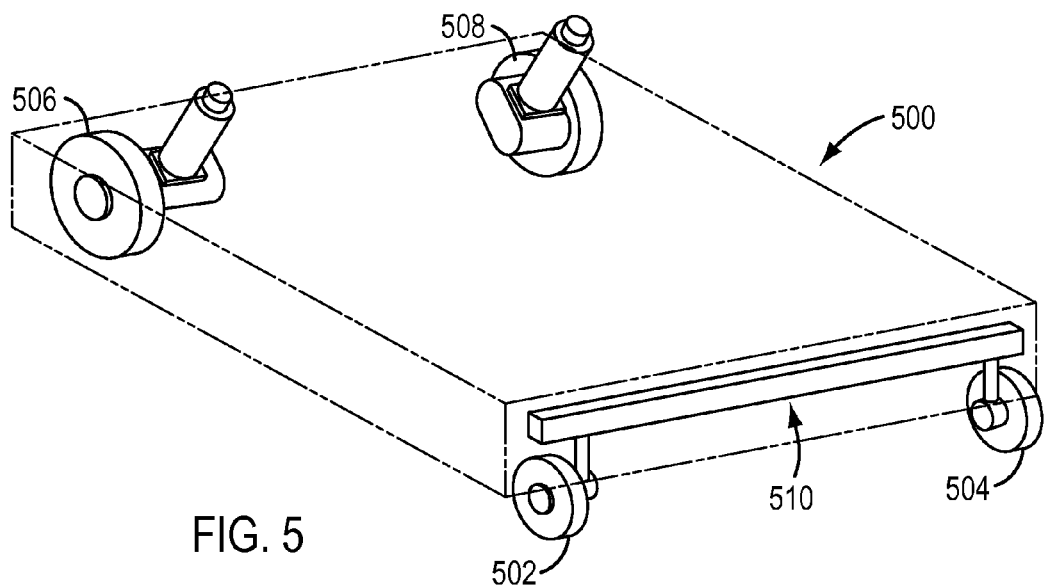
FIG. 5 is a perspective view of an exemplary embodiment of a base of a patient side cart with a suspension system according to an exemplary embodiment of the present disclosure.

In view of the issues described above, it may be desirable to provide a patient side cart having enhanced stability. For instance, a patient side cart could have enhanced stability when the cart is on an irregular ground surface and in a deployed configuration. Turning to FIG. 5, an exemplary embodiment of a base 500 of a patient side cart is shown that has a pivotable suspension system 510 in accordance with one exemplary embodiment of the present disclosure. The pivotable suspension system may be configured according to the various exemplary embodiments described herein and used with the various patient side cart exemplary embodiments described herein, with the patient side cart 110 of FIG. 1 being one non-limiting exemplary embodiment. For instance, base 500 may correspond to the base 148 of the patient side cart 110 shown in the exemplary embodiment of FIG. 1. Base 500 may be an integral part of a patient side cart, and thus may have a single-piece construction with the cart, or the base 500 may be a separate piece that is attached to a patient side cart.

Base 500 may include a plurality of wheels to provide movement to a patient side cart. For instance, a base 500 may include a left front wheel 506, a right front wheel 508, a left rear wheel 502, and a right rear wheel 504, somewhat similar to wheels 202, 204, 206, 208 of the embodiment of FIG. 2 with distinctions being explained below. One or more of the wheels 502, 504, 506, 508 of a patient side cart 500 may be driven by a drive system included in the patient side cart 500 that provides motive force to the driven wheel(s). For instance, patient side cart 500 may include a drive system that is configured, for example, as described in U.S. application Ser. No. 14/209,239 entitled "Surgical Patient Side Cart with Drive System and Method of Moving a Patient Side Cart," filed on Mar. 13, 2014, which is hereby incorporated by reference in its entirety. Driven wheels may be prevented from turning relative to a vertical axis or driven wheels may be turned relative to a vertical axis according to a user's desire to move a patient side cart in a given direction.

In the exemplary embodiment of FIG. 5, front wheels 506, 508 may be driven, such as by a drive system that is operative, for example, in response to user activation as described further below. Thus, motive force may be provided to front wheels 506, 508 to move a patient side cart 500 in a desired direction (e.g., including fore and aft). Furthermore, driven wheels, such as front wheels 506, 508, may be driven at different speeds, such as to provide a torque to a patient side cart 500 and cause the cart 500 to turn in desired direction. Rear wheels 502, 504 may be free to rotate and turn about a vertical axis. For example, rear wheels 502, 504 may be caster wheels, such as heavy duty caster wheels. Further, while front wheels 506, 508 may be driven, rear 502, 504 need not be driven.

According to an exemplary embodiment, front wheels 506, 508 and rear wheels 502, 504 may be located in similar locations in a side-to-side or left to right direction. According to another exemplary embodiment, front wheels 506, 508 and rear wheels 502, 504 may be located in different left to right locations. For instance, front wheels 506, 508 may be set further apart than rear wheels 502, 504, or front wheels 506, 508 may be set closer together than rear wheels 502, 504. In one exemplary embodiment of a patient side cart, front wheels 506, 508 may have a front wheelbase of, for example, approximately 31 inches.

According to an exemplary embodiment, a patient side cart may include a device that receives input from a user indicating what direction the user would like the patient side cart to move in. The device may receive input from a user, such as by detecting the amount of force a user applies to the device in a fore or aft direction. For instance, a patient side cart 200 of a teleoperated surgical system may include a steering interface (not shown) by which the user activates the drive system of the patient side cart 200. A steering interface may be configured as described in U.S. application Ser. No. 14/208,663 entitled "Surgical Patient Side Cart with Steering Interface," filed on Mar. 13, 2014, which is hereby incorporated by reference in its entirety.

A steering interface may be used to detect forces applied by a user to the steering interface, which in turn may issue one or more signals to a controller of a drive system of a patient side cart, which in turn causes the patient side cart to be driven and steered in a desired manner. A steering interface may be attached, for example, to a rear of a patient side cart, with one or more surgical instrument(s) being located over a front end portion of the patient side cart. However, the exemplary embodiments described herein are not limited to a patient side cart with a steering interface attached to a rear, and the steering interface may instead be mounted on other portions of a patient side cart, such as a front or side of a patient side cart.

Figure 6:
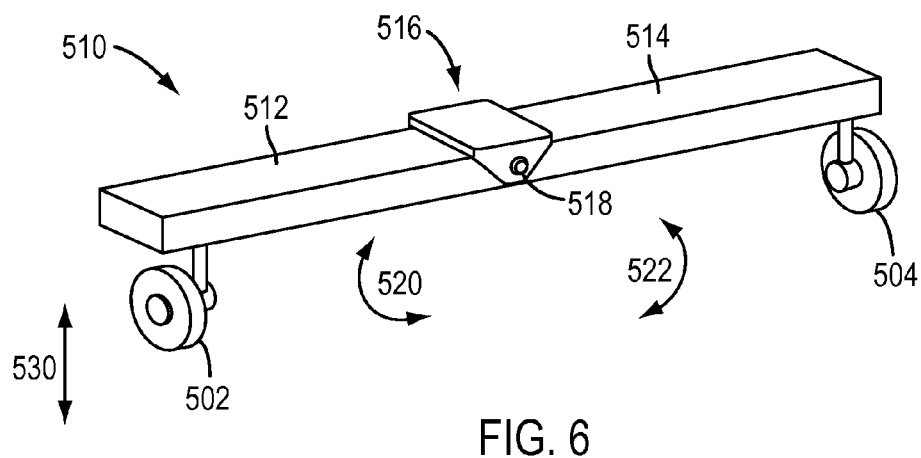
FIG. 6 is a perspective view of an exemplary embodiment of suspension system for a patient side cart in accordance with the present disclosure.

According to an exemplary embodiment, rear wheels 502, 504 may be mounted to or included in a pivotable suspension system 510, as shown in detail in the exemplary embodiment of FIG. 6. Suspension system 510 may permit relative movement between rear wheels 502, 504 and a patient side cart, such as the base 500 of the exemplary embodiment of FIG. 5, upward or downward in a substantially vertical direction, such as direction 530 in the exemplary embodiment of FIG. 6. To provide such a relative movement, the suspension system 510 may include an arm 511 that wheels 502, 504 are mounted or otherwise attached to, with the arm 511 pivoting about a point. According to an exemplary embodiment, the pivot point for the arm 511 may be an attachment point for attaching the suspension 510 to a patient side cart, such as a base 500 of a cart.

As shown in FIG. 6, arm 511 may include a first arm portion 512 that wheel 502 is attached to and a second arm portion 514 that wheel 504 is attached to. According to an exemplary embodiment, arm 511 may be formed with a single piece construction, with first arm portion 512 and second arm portion 514 being formed as a single arm piece.

Arm 511, including arm portions 512, 514 may be formed, for example, from welded steel. For instance, arm portions 512, 514 may be formed, for example, from 0.25 inch thick steel sections welded together. Wheels 502, 504 may be attached to the first and second arm portions 512, 514 by, for example, brackets (not shown) respectively, or by other devices or means used in the art to attach wheels in a durable manner.

According to an exemplary embodiment, any wheels of a patient side cart may be mounted to a pivotable suspension system, including the front wheels of a patient side cart. Further, some of the wheels of a patient side cart may be mounted to a suspension system or all wheels of a cart may be mounted to a suspension system. According to an exemplary embodiment, driven front wheels 506, 508 may be separated from or otherwise not directly attached to or supported by suspension system 510, as shown in FIG. 5.

First arm portion 512 and second arm portion 514 may be joined at a central portion 516 of the suspension system 510. Central portion 516 may form a pivot or pivot axis for arm 511, such as by including a structure to permit pivoting of the first arm portion 512 and the second arm portion 514 about a point. The pivot provided by central portion 516 may be an axis substantially extending in a forward-backward direction of a patient side cart. Thus, arm portions 512, 514 and central portion 516 may form a rocker arm assembly. For instance, as shown in the exemplary embodiment of FIG. 6, the central portion 516 of suspension system 510 can include a shaft 518 that the arm portions 512, 514 are attached to and about which the arm portions 512, 514 pivot. Shaft 518 may have a diameter of, for example, approximately 1 inch. Shaft 518 may be housed within a bushing (not shown) of the central portion 516.

Arm portions 512, 514 may pivot about central portion 516, such as in directions 520 and 522 in FIG. 6 to provide a relative movement between wheels 502, 504 and a patient side cart. Although such a relative movement may follow an arc, a user of a patient side cart may perceive the relative movement as movement in a substantially vertical direction 530 shown in FIG. 6. Such a relative movement may be perceived by a user of a patient side cart as movement by the cart in the substantially vertical direction 530 or movement by one or more of the wheels 502, 504 in the substantially vertical direction, depending on whether the user's point of reference is a stationary ground surface or the cart as being stationary. In one example, arm portions 512, 514 may pivot about central portion 516 by approximately +/−2.25 degrees to provide a relative movement between at least one of the wheels 502, 504 and a patient side cart.

Although wheels 506, 508 may be at fixed positions relative to a ground surface, wheels 502, 504 may be attached to a pivotable suspension 510 that permits a relative movement between wheels 502, 504 and a cart by permitting arm 511 of the suspension system 510 and wheels 502, 504 to pivot about central portion 516. Because wheels 502, 504 may pivot relative to the central portion 516 to provide this relative movement, central portion 516 may remain relatively stationary to a ground surface. Thus, loads may be transferred through the central portion 516 of a pivoting suspension, thereby enabling the cart to behave as if it has a stationary point of contact with a ground surface proximate the central portion 516. As a result, pivotable suspension system 510 may provide a cart with the stiffness and stability of a three-wheeled configuration even though the cart includes four wheels 502, 504, 506, 508. However, as will be discussed below, the cart may also act like a four-wheeled cart in another state. One of ordinary skill in the art will thus appreciate that suspension systems in accordance with various exemplary embodiments therefore do not behave in all circumstances like a conventional suspension system of an automobile, although under some conditions of the cart, the suspension system of various exemplary embodiments of the present disclosure permit the cart to have the benefits of the stability of a four-wheeled vehicle (e.g., an automobile).

The pivot axis (e.g., shaft 518) may be centered between and aligned with the wheels 502 and 504 (horizontally and/or vertically). However, in various other embodiments the pivot axis for suspension system 510 can be positioned at any location relative to wheels 502 and 504. For example, in some embodiments, suspension system 510 can position shaft 518 above or below the axes of rotation of wheels 502 and 504. In some embodiments, a pivot axis above the center of mass of the cart can reduce the propensity of the cart to topple over. In other embodiments, the pivot axis of suspension system 510 can be positioned fore or aft of the vertical axis of rotation of wheels 502 and 504. In various other embodiments, the pivot axis of suspension system 510 can be angled with respect to the plane of the wheel axes (i.e., angled with respect to the plane formed by the axes of the cart wheels). In addition, in some embodiments suspension system 510 can include a locking mechanism to selectably prevent pivoting about shaft 518 (e.g., to maintain a fixed orientation for the cart once it is in a desired location). Such a locking mechanism may engage shaft 518 directly, or may interface with the surrounding support structure (e.g., central portion 516 and arm portions 512 and 514).

In various exemplary embodiments, one or more devices may be used to control the stability and behavior of a cart, particularly in view of the teetering and traction issues discussed above with regard to the exemplary embodiments of FIGS. 2 and 4. Further, as will be discussed below, a cart may be configured to act in one state like a three-wheeled cart and act in another state like a four-wheeled cart. One or more devices may be used to control a transition of cart behavior between acting like a three-wheeled cart and a four-wheeled cart. For instance, one or more devices may act to provide a relatively smooth transition, making it less abrupt and/or jarring to a user of a cart.

Figure 7:
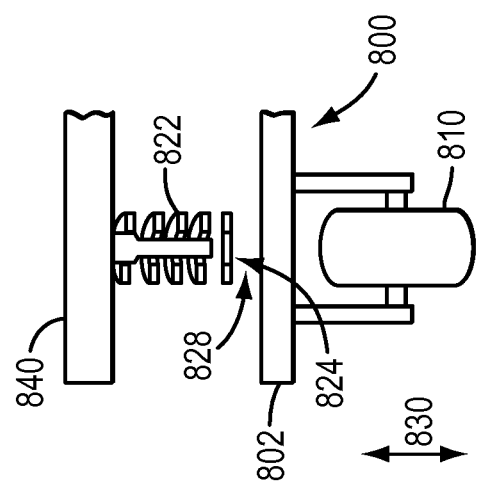
FIG. 7 is a partial perspective view of the suspension system of FIG. 6 showing a wheel in contact with a level ground surface.

Turning to FIG. 7, an exemplary embodiment of a wheel 810 and a pivotable suspension system 800 is shown when the wheel 810 is in contact with a level ground surface (not shown). Pivotable suspension system 800 may have the features of the exemplary embodiment of pivotable suspension system 510 of FIG. 6. For instance, pivotable suspension system may include an arm, such as arm 511 pivotable suspension system 510 of FIG. 6, with the wheel 810 attached to arm portion 802 thereof. According to an exemplary embodiment, wheel 810 may be attached to the arm portion 802 by a bracket (not shown) or other means or devices used to attach wheels.

In addition, pivotable suspension system may include one or more devices to affect the movement of the wheel 810. For instance, a device may be an impact reduction mechanism used to reduce to reduce the angular velocity of a wheel 810 and arm portion 802 as the suspension system pivots so that the arm portion 802 does not impact a patient side cart at a high angular velocity when the arm portion 802 reaches its limit of travel during pivoting of the suspension system. An impact reduction mechanism may include a compliant member, such as a spring 822, although spring 822 is a non-limiting example and one of ordinary skill in the art would appreciate that other compliant members could be used. For example, a viscoelastic material (e.g., foam) could be used. Spring 822 may have a spring rate of, for example, approximately 500 pounds per inch. According to an exemplary embodiment, spring 822 may be fastened to a bottom portion of a patient side cart, such as a base 840. According to an exemplary embodiment, an impact reduction mechanism may include a damping device to absorb energy from the movement of a wheel relative to a patient side cart. A damping device may be, for example, a hydraulic cylinder that pushes fluid through an orifice, a viscoelastic material, or other damping device recognized by one of ordinary skill in the art. According to an exemplary embodiment, a damping device may be provided in addition to a spring 822 or other compliant member used to reduce an angular velocity between a wheel and a patient side cart.

When a patient side cart having a pivotable suspension system 800 is located on a level, regular ground surface, an impact reduction mechanism, such as spring 822, may be in a disengaged position and thus not affect the movement of the wheel 810. According to an exemplary embodiment, when a patient side cart including a pivotable suspension system 800 is located on a level ground surface, as shown in the exemplary embodiment of FIG. 7, the impact reduction mechanism may not be in contact with the arm member 802 of the pivotable suspension system 800. For instance, a bottom surface 824 of the spring 822 may be configured to come into contact with the arm member 802 when wheel 810 moves a sufficient distance in a substantially vertical direction 830. According to an exemplary embodiment, a gap 828 may be present between a bottom surface 824 of spring 822 and arm member 802, as shown in the exemplary embodiment of FIG. 7. Thus, relative movement may be freely permitted between wheel 810 and arm member 802 in the substantially vertical direction 830 before engagement is made with an impact reduction mechanism. According to an exemplary embodiment, the distance of gap 828 may be selected to exceed a height of any ground protuberances or divots that may be encountered, which may maintain full contact between the front driven wheels and may provide maximum traction for steering, as described above. For instance, gap 828 may be selected to exceed a height of ground protuberances or divots normally encountered in standard indoor hospital environments.

When a patient side cart having a pivotable suspension system 800 is on an inclined ground surface or on an irregular ground surface that includes protuberances and/or depressions, relative movement may occur between a wheel 810 and a patient side cart in a substantially vertical direction. For instance, relative movement may occur between wheel 810 and the cart in the substantially vertical direction 830 shown in the exemplary embodiment of FIG. 7. When this occurs and the movement between wheel 810 and the cart is large enough, a bottom surface 824 of the spring 822 may come into contact with the arm member 802 of the pivotable suspension system 800, as shown in the exemplary embodiment of FIG. 8. According to an exemplary embodiment, a relative movement may occur between wheel 810 and a patient side cart, such as base 840, over a distance of approximately 0.3 inches in the substantially vertical direction 830 before arm member 802 contacts spring 822. In other words, gap 828 between the bottom surface 824 of spring 822 and arm member 802 may be approximately 0.3 inches when a cart including a pivotable suspension system 800 is located on a substantially level ground surface.

Figure 8:
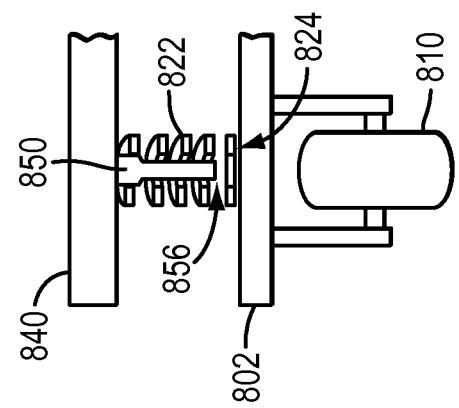
FIG. 8 is a partial perspective view of the suspension system of FIG. 6 showing a spring member of the suspension system in an engaged position.

When an impact reduction mechanism engages an arm member 802, such as when spring 222 engages an arm member 802, as shown in the exemplary embodiment of FIG. 8, the impact reduction mechanism may affect the relative movement between a wheel 810 and a patient side cart, such as by reducing the angular velocity of wheel 810. For instance, spring 822 may become compressed and resist motion when the wheel 810 and the base 840 of the patient side cart move closer to one another, as shown in FIG. 8, resulting in a reduced angular velocity between wheel 810 and the patient side cart. Thus, an impact reduction mechanism may provide a relatively smooth movement between a wheel and a patient side cart by resisting the relative movement to some degree. For instance, if a pivotable suspension system did not include impact reduction mechanisms as described above, the relative movement between the wheel and the cart could provide a jarring sensation and even a loud noise when the relative movement allowed by a pivotable suspension system has reached its limit and a stop is suddenly impacted. One or more impact reduction mechanisms may act to counter this by resisting the relative movement when the impact reduction mechanism is engaged, providing relatively slower, smoother movements until the maximum travel has been reached. Such an effect can advantageously provide a less alarming experience for a user of a cart and improve user experience.

Figure 9:
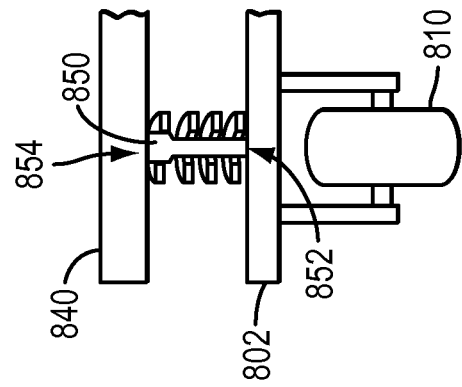
FIG. 9 is a partial perspective view of the suspension system of FIG. 6 showing a stop of the suspension system in an engaged position.

A pivotable suspension system may include one or more devices to limit the amount of relative movement permitted between a wheel and a patient side cart. Turning to FIG. 9, an exemplary embodiment of a pivotable suspension system 800 with a wheel 810 is shown when a stop 850 of the pivotable suspension system 800 has been engaged. For instance, a patient side cart including the pivotable suspension system may be located on irregular terrain and/or deployed in an state shifting a center of mass of the cart, causing relative movement between the wheel 810 and the cart in a substantially vertical direction 830 so that wheel 810 and the base 840 of a patient side cart may move closer to one another. After an impact reduction mechanism, such as spring 822, has been engaged, as shown in the exemplary embodiment of FIG. 8, the relative movement between the wheel 810 and the cart may continue in the substantial vertical direction 830. To limit this movement and the destabilization of a patient side cart, the pivotable suspension system 800 may include one or more stops 850.

According to an exemplary embodiment, stop 850 may be formed by a member, such as a pin or rod, located between arm member 802 and the patient side cart, such as the base 840 of the cart, as shown in FIG. 9. Further, stop 850 may be located within spring 822, as shown in FIG. 9. As shown in the exemplary embodiment of FIG. 9, stop 850 may engage the arm member 802 to stop movement of the wheel 810. In particular, a bottom surface 852 of stop 850 may engage the arm member 802 and a top surface 854 of stop 850 may engage the patient side cart or the base 840 of the cart, as shown in the exemplary embodiment of FIG. 9. Prior to the stop 850 engaging the arm member 802, a gap 856 may be provided between the stop 850 and the arm member 802, as shown in the exemplary embodiment of FIG. 8. Gap 856 may provide a distance of, for example, approximately 0.20 inches to approximately 0.35 inches. In another example, gap 856 may provide a distance of, for example approximately 0.30 inches. Thus, wheel 810 and arm member 810 may travel a distance of approximately 0.2 inches to approximately 0.35 inches after spring 822 has been engaged and before stop 850 is engaged.

According to an exemplary embodiment, a pivotable suspension system 800 may include a plurality of stops for a single wheel 810. For instance, a pivotable suspension system 800 may include a first stop 850, as described above, and a second stop (not shown) to limit the relative movement between the wheel 810 and a patient side cart. Second stop may be provided as a projection on arm member 802 that engages a portion of the patient side cart. By providing a plurality of stops for limiting the relative movement between a wheel 810 and a patient side cart, redundant safety devices may be provided so that if one stop fails, such as first stop 850, another stop, may still be used to limit relative movement between a wheel and the cart.

Figure 10:
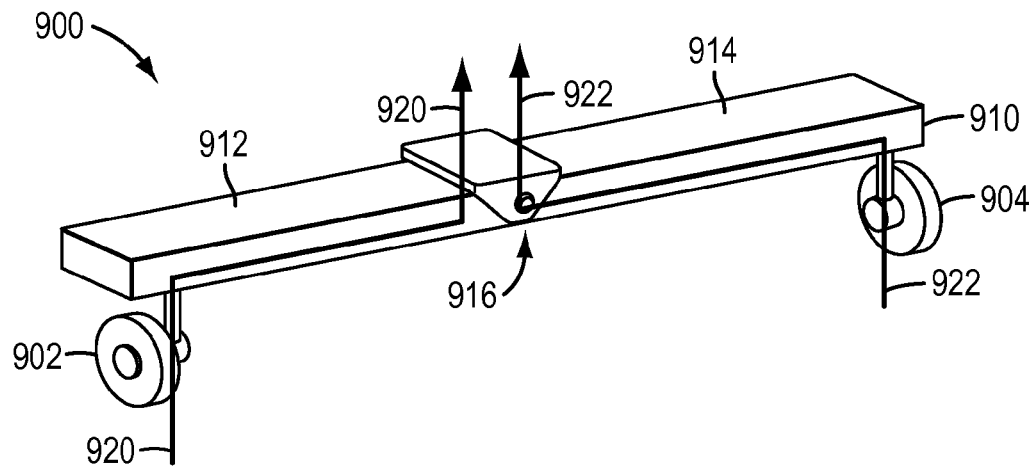
FIG. 10 is a perspective view of an exemplary embodiment of a suspension system for a patient side cart, showing a load path when the patient side cart is on a level ground surface in accordance with the present disclosure.

Turning to FIG. 10, an exemplary embodiment of a pivotable suspension system 900 is shown in a state corresponding to a patient side cart including the pivotable suspension system 900 being located on a level ground surface. Pivotable suspension system 900 may have the features of the exemplary embodiments of FIGS. 6-9, including an arm 910 that may include a first arm member 912, a second arm member 914, and a central portion 916. In the state of FIG. 10, impact reduction mechanisms and stop(s) of the pivotable suspension system 900 are not engaged. As a result, forces applied to the pivotable suspension system via wheels 902, 904 are distributed through the pivotable suspension system 900. For instance, as shown in the exemplary embodiment of FIG. 10, a load path 920 for a force applied to wheel 902 may extend from wheel 902 through pivotable suspension system 900, such as along arm member 912, to a central portion 916 where the pivotable suspension system 900 may be attached to a patient side cart, such as a base (not shown) of a cart. Similarly, a load path 922 for a force applied to wheel 904 may extend from wheel 904 through pivotable suspension system 900, such as along an arm member 914, to the central portion 916 and then on to a base (not shown) of a cart. Thus, the pivotable suspension system 900 may sustain the forces applied to the wheels attached to the pivotable suspension system 900 when any stops and/or impact reduction mechanisms of the pivotable suspension system are not engaged. According to an exemplary embodiment, when forces are transmitted along load paths 920, 922, a cart may behave like a three-wheeled cart even though the cart includes four wheels, with central portion 916 (where cart and suspension system 900 pivot relative to one another) bearing a load like a third wheel in contact with a ground surface would.

When either an impact reduction mechanism or a stop for a pivotable suspension system is engaged, however, a different load path may be provided so the forces applied to a wheel are not distributed through the pivotable suspension system. For instance, a load path may be provided so forces are not distributed along an arm member and through a central portion of the pivotable suspension system. Routing a load path to avoid distributing forces along the arm member and through the central portion of a pivotable suspension system may advantageously minimize or avoid failure of pivotable suspension system components due to the excessive forces applied to a pivotable suspension system, such as forces significant enough to cause a stop of the pivotable suspension system to be engaged.

Figure 11:
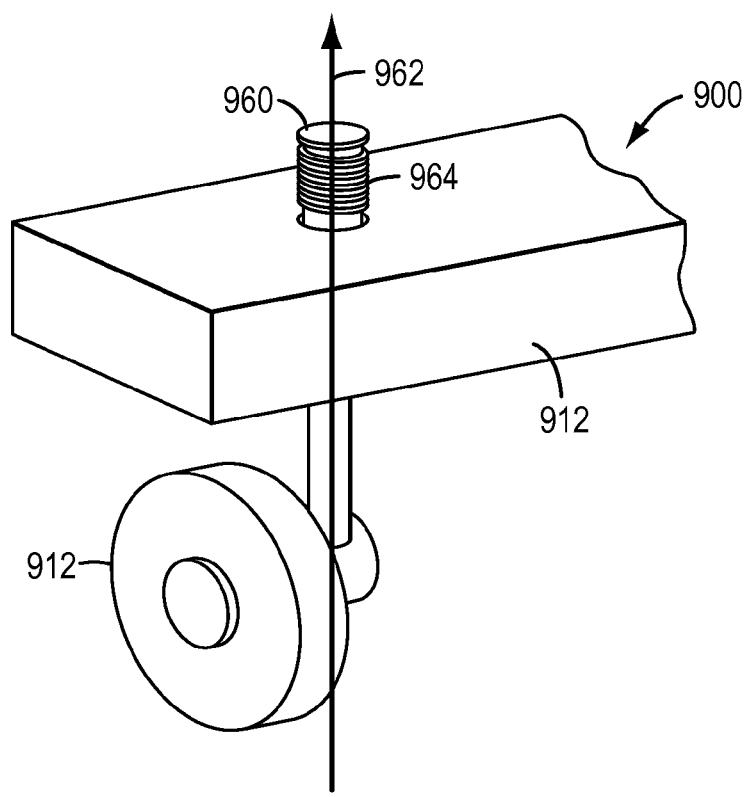
FIG. 11 is a partial perspective view of the suspension system, showing a load path when a stop of the suspension system is in an engaged position in accordance with the present disclosure.

Turning to FIG. 11, an exemplary embodiment of a pivotable suspension system 900 is shown when a spring 964 and/or a stop 960 of the pivotable suspension system is engaged. When the spring 964 and/or the stop 960 is engaged, a load path 962 may be provided in which a force is applied to wheel 902, through arm member 912, spring 964 and/or stop 960, and then to base (not shown), as shown in FIG. 11. According to an exemplary embodiment, when stop 960 is engaged with arm member 912 and forces are transmitted along load path 962, a cart may behave like a four-wheeled cart, and when stop 960 is not engaged and forces are transmitted along paths 920, 922 through a central portion 916, as depicted in FIG. 10, the cart may behave like a three-wheeled cart.

Figure 12:
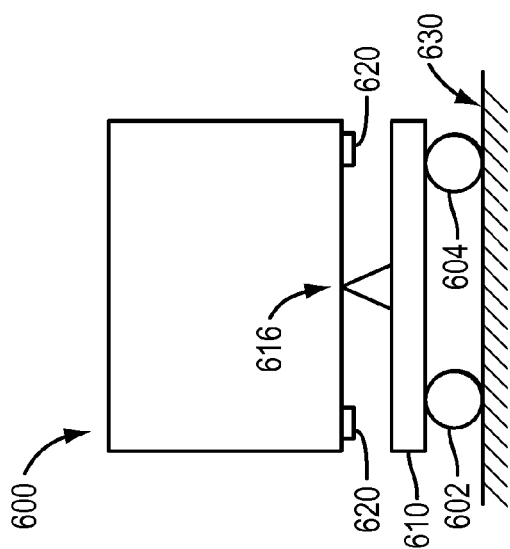
FIG. 12 is a schematic end view of an exemplary embodiment of a cart with a suspension system in a stationary position on a level ground surface in accordance with the present disclosure.

A patient side cart provided with a suspension system according to the embodiments described above can provide a stiff, stable base for components mounted to the cart, such as during use of the cart when the cart is in a stationary position, while also providing enhanced stability, such as during movement of the cart from one location to another or when a center of mass of the cart is shifted to a large degree. Turning to FIG. 12, an end view of a patient side cart 600 is shown that includes a suspension system as described with respect to various exemplary embodiments herein. Cart 600 may include four wheels, such as wheels 602, 604 attached to the suspension system and two other wheels not shown (such as wheels 706, 708 shown in the exemplary embodiment of FIG. 15) that are not attached to the suspension system. The suspension system may be configured according to the exemplary embodiments of FIGS. 5-11. For instance, suspension system may include an arm 610, a central portion 616, and stops 620. The cart 600 and suspension system are advantageously stiff and stable when cart 600 is in a stationary position on a ground surface 630, such as during a surgical procedure, for example. According to an exemplary embodiment, when cart 600 is in the state shown in the exemplary embodiment of FIG. 12, cart may act like a three-wheeled cart. For instance, because stops 620 are not engaged with arm 610, central portion 616 may act like a third wheel (besides two other wheels not shown, such as wheels 706, 708 shown in the exemplary embodiment of FIG. 15 that are not attached to the suspension system). Further, forces transmitted through wheels 602, 604 to suspension system may be transmitted through central portion 616, such as described above with reference to FIG. 10.

Figure 13:
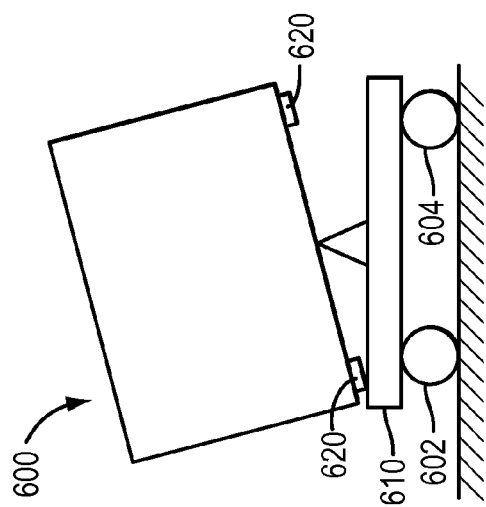
FIG. 13 is a schematic end view of an exemplary embodiment of a cart with a suspension system in an extreme deployed configuration in accordance with the present disclosure.

Turning to FIG. 13, the patient side cart 600 of FIG. 12 is shown but in a state in which the center of mass of cart 600 has shifted to one side, such as when cart 600 is in a stationary position. For instance, a center of mass may be shifted to one side because components of the cart have been configured and deployed in an extreme position or because the cart is located on a smooth, inclined surface. As a result, cart 600 may lean to one side but the enhanced stability provided by the suspension system may prevent tipover of cart 600. As shown in the exemplary embodiment of FIG. 13, a stop 620 of the suspension system may engage the arm 610 of the suspension system to limit leaning of cart 600 and prevent tipover. Further, because stop 620 and arm 610 are engaged with one another, cart 600 may act like a four-wheeled cart between wheels 602, 604 and the wheels not shown (such as wheels 706, 708 shown in the exemplary embodiment of FIG. 15). In addition, forces may be transmitted through wheels 602, 604 to stop 620 engaged with arm 610, as described above with reference to FIG. 11.

Figure 14:
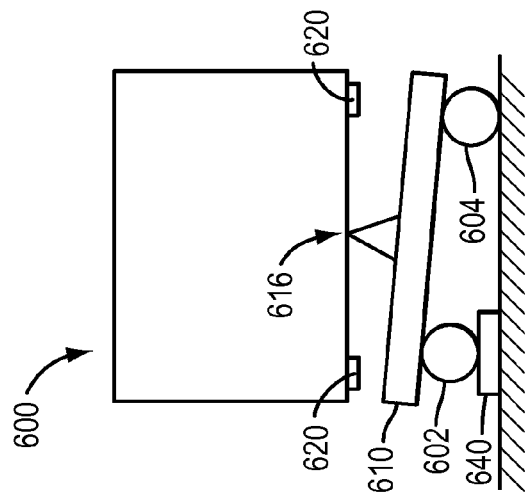
FIG. 14 is a schematic end view of an exemplary embodiment of a cart with a suspension system traversing an irregular ground surface in accordance with the present disclosure.

Further, cart 600 and the suspension system may advantageously maintain traction between wheels and a ground surface. For instance, cart 600 may maintain traction between all of its wheels during movement of cart 600 over an irregular ground surface from one location to another. Turning to FIG. 14, the patient side cart 600 of FIG. 12 is shown in a state in which wheel 602 of cart 600 is traversing over and in contact with a protuberance 640, causing wheel 602 and arm 610 to pivot and move relative to central portion 616 and the remainder of cart 600. However, because wheel 601 and arm 610 pivot, other wheels of cart 600 (e.g., wheel 604 and wheels not shown, such as wheels 706, 708 shown in the exemplary embodiment of FIG. 15) maintain contact and traction with the ground surface.

Conversely, if cart 600 did not include the suspension system, cart 600 would behave like cart 400 in the exemplary embodiment of FIG. 4 and one wheel would lose contact and traction with the ground surface, which could affect driving and steering of the cart. Thus, by providing a cart with a suspension system that maintains contact and traction between cart wheels and a ground surface, a user is provided with enhanced control when moving the cart over irregular ground surface.

Figure 15:
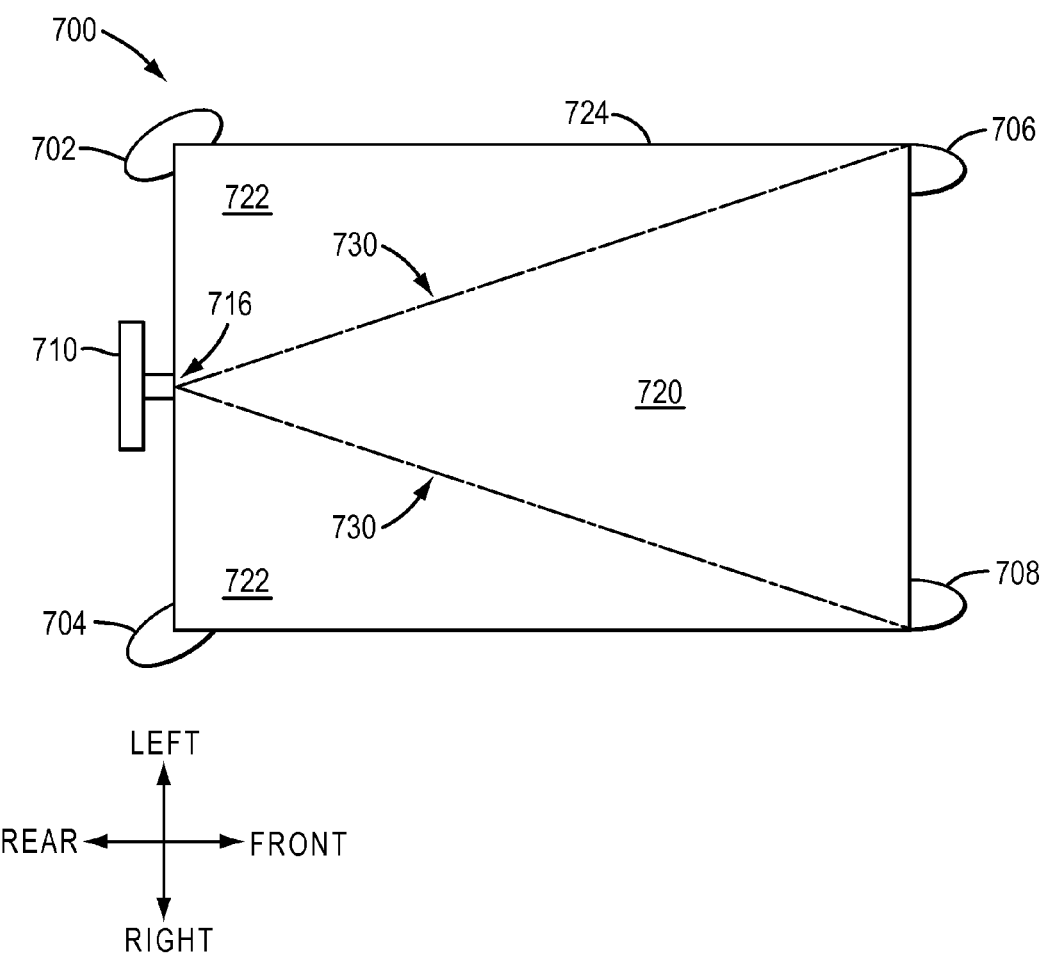
FIG. 15 is a schematic top view illustrating various stability zones of an exemplary embodiment of a cart having a suspension system in accordance with the present disclosure.

As discussed above, a pivotable suspension system permits a cart to behave under certain conditions like a cart with three wheels even though the cart has four wheels. Turning to FIG. 15, a schematic top view of stability zone projections is shown for a patient side cart 700 having a suspension system in accordance with various exemplary embodiments of the present disclosure. Patient side cart 700 can be configured according to various exemplary embodiments as described herein, with the patient side cart 110 of FIG. 1 being one non-limiting exemplary embodiment. Patient side cart 700 may include wheels 702, 704, 706, 708, which may be configured according to the exemplary embodiment of FIG. 2. Patient side cart 700 includes a pivotable suspension system with a pivoting arm to support wheels 702, 704, such as a suspension system 510 as shown in the exemplary embodiments of FIGS. 5-11. Although the suspension system is not shown in FIG. 15, the location of a central portion 716 of the suspension system is indicated in FIG. 15, which may correspond substantially to central portion 516 shown in the exemplary embodiment of FIG. 6. Further, patient side cart 700 may include a steering interface 710. Steering interface 710 may be configured as described in U.S. application Ser. No. 14/208,663 entitled "Surgical Patient Side Cart with Steering Interface," filed on Mar. 13, 2014, incorporated by reference herein.

When the stops of the suspension system of cart 700 are not engaged, such as in the states shown in the exemplary embodiments of FIGS. 7, 10, 12, and 14, cart 700 may act like a three-wheeled cart, with wheels 706, 708 and central portion 716 of the suspension system acting as the three wheels. In other words, the load distributions provide the cart 700 with the stability of a three-wheel cart. In such a state, the suspension system permits relative movement between wheels 702, 704 and the remainder of cart 700, advantageously permitting traction to be maintained between wheels 702, 704, 706, 708 and a ground surface, as discussed above with regard to the exemplary embodiment of FIG. 14. When cart 700 provides the stiffness of a three-wheeled cart, area 720 in FIG. 15 serves as a zone of stability, which is bounded by the front edge of rectangle 724 and boundaries 730. Further, stops of the suspension system are not engaged with an arm of the suspension system, as discussed above in regard to the exemplary embodiments of FIGS. 7, 10, 12, and 14.

As discussed above in regard to the exemplary embodiment of FIG. 2, the stability zones shown in FIG. 15 are examples and may vary in size and/or shape from what is shown in FIG. 15. For instance, the position and size of area 720 and the position of boundaries 730 may vary, such as due to change of positions of contact areas between wheels and a ground surface.

According to an exemplary embodiment, cart 700 acts like a three-wheeled cart while a center of mass of cart 700 remains within area 720. When a center of mass of cart 700 is located outside of rectangle 724 the cart 700 is in a tipover state. However, boundaries 730 may also signify a tipover point for a three-wheeled configuration. Thus, if a center of mass of cart 700 should shift from area 720 over a boundary 730 into an area 722 in FIG. 15, a three-wheeled cart would normally be unstable and tipover. However, because cart 700 includes four wheels 702, 704, 706, 708 and the suspension system, the suspension system may permit relative movement between wheels 702, 704 and cart 700 when the center of mass shifts to one of zones 722 in FIG. 15 until a stop (not shown) of the suspension system is engaged, which limits the relative movement between wheels 702, 704 and cart 700. Once a stop has been engaged, as discussed above in the exemplary embodiments of FIGS. 9, 11, 13, cart 700 may act like a four-wheeled cart that advantageously has enhanced tipover resistance in comparison to a cart having three-wheels would. Thus, cart 700 may advantageously provide the benefits of stiffness and traction provided by a three-wheeled cart configuration and the benefits of enhanced stability provided by a four-wheeled cart configuration.

By providing a patient side cart with a pivotable suspension system according the exemplary embodiments discussed above, stability of the patient side cart may be advantageously improved. For instance, a cart may be stiff and stable when the suspension system is in a configuration that enables the cart to behave as a three-wheeled cart, such as on a flat ground surface. Also, the suspension system may be compliant and permit transition to a configuration that enables the cart to behave as a four-wheeled cart, such as when the cart is on an uneven ground surface or otherwise may benefit from having four wheels in contact and traction with a ground surface.

According to one example, a patient side cart including a pivotable suspension system may remain stable and not overbalance on up to a 5 degree incline when in a deployed configuration. In another example, a patient side cart including a pivotable suspension system may remain stable and not overbalance on up to a 10 degree incline when in a stowed configuration. In another example, a patient side cart including a pivotable suspension system may remain stable and not tipover when a force up to 220 Newtons (50 pound) is applied to the cart, the cart is on a level ground surface, and the cart is in a deployed configuration. In another example, a patient side cart including a pivotable suspension system may remain stable and not tip over when the cart is on up to a 1.5 degree incline, in a deployed configuration, and up to a 50 pound force is applied to the cart. In another example, a patient side cart including a pivotable suspension system may remain stable and move according to a desired manner when in a deployed configuration and on up to a 1.5 degree incline. Further, a patient side cart with a pivoting suspension may advantageously permit driven wheels to maintain traction with ground surface, which permits cart to be driven and turned in desired manner.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

According to an exemplary embodiment, a suspension system may permit relative movement between a patient side cart and a wheel without using a pivoting movement or action. For instance, one or more wheels of a patient side cart can be mounted to the cart via one or more force absorption mechanisms that permit relative movement between the wheel and the cart. Force absorption mechanisms can be, for example, one or more springs or other force absorption mechanisms.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the claims being entitled their full breadth of scope, including equivalents.

What is claimed is:

1. A patient side cart for a teleoperated surgical system, comprising:
   a base; and
   a manipulator portion extending from the base and configured to hold one or more surgical instruments, the manipulator portion being movable between a compact configuration and an extended configuration, wherein the patient side cart has a center of mass in the compact configuration of the manipulator portion;
   a first wheel and a second wheel; and
   oppositely extending arm portions that support the first wheel and the second wheel, the arm portions being pivotable toward and away from the base about an axis, the axis being disposed between the arm portions and above the center of mass of the patient side cart.

2. The patient side cart of claim 1, wherein the arm portions comprise a first arm portion to which the first wheel is mounted and a second arm portion to which the second wheel is mounted.

3. The patient side cart of claim 2, further comprising a third wheel and a fourth wheel, wherein the third wheel and the fourth wheel are driven wheels.

4. The patient side cart of claim 3, wherein the third wheel and the fourth wheel are mounted to the base and not supported by the arms.

5. The patient side cart of claim 2, wherein the first arm portion and the second arm portion join together at a central portion through which the axis passes.

6. The patient side cart of claim 5, wherein the central portion is mounted to the base.

7. The patient side cart of claim 5, further comprising a shaft located at the central portion and about which the first arm portion and the second arm portion are pivotable.

8. The patient side cart of claim 1, wherein the first and second wheels are caster wheels.

9. The patient side cart of claim 1, further comprising impact reduction mechanisms disposed between the wheels and the base, wherein the impact reduction mechanisms are configured to reduce an angular velocity between the wheels and the base.

10. The patient side cart of claim 9, wherein the impact reduction mechanisms comprise a first spring and a second spring respectively disposed between the first wheel and the base and the second wheel and the base.

11. The patient side cart of claim 9, wherein the impact reduction mechanisms are spaced from the respective arm portions when the patient side cart is located on a level ground surface.

12. The patient side cart of claim 11, wherein the impact reduction mechanisms are configured so that a load path for a force applied to the wheels extends from the wheels through the arm portions to the axis disposed between the arm portions when the impact reduction mechanisms are spaced from the respective arm portions;
   wherein the impact reduction mechanisms are configured so that the load path for the force applied to the wheels extends from the wheels through the arm portions to the impact reduction mechanisms when the impact reduction mechanisms engage the respective arm portions.

13. The patient side cart of claim 1, further comprising a first set of stops disposed to limit pivoting movement between the arm portions and the base.

14. The patient side cart of claim 13, wherein the stops and the respective opposing arm portions contact each other to limit the pivoting movement between the arm portions and the base.

15. The patient side cart of claim 14, wherein the stops are spaced from the respective arm portions when the patient side cart is located on a level ground surface.

16. The patient side cart of claim 13, further comprising a second set of stops disposed to limit the pivoting movement between the respective opposing arm portions and the base.

17. The patient side cart of claim 1, further comprising third and fourth wheels, wherein the first and second wheels are disposed at a first end portion of the base and the third and fourth wheels are disposed at a second end portion of the base opposite the first end portion.

18. The patient side cart of claim 17, wherein the first end portion and the second end portion are positioned relative to each other in an aft-to-fore direction of motion of the cart.

19. A patient side cart for a teleoperated surgical system, comprising:
   a base;
   a manipulator portion extending from the base and configured to hold one or more surgical instruments;
   four wheels mounted to the base to permit movement of the cart; and
   a suspension system configured to permit passive motion of two of the wheels relative to the cart in response to forces acting on the cart, the passive motion transitioning the cart between a first state wherein a stability of the cart is that of a three-wheeled cart and a second state wherein the stability the cart is that of a four-wheeled cart, the suspension system comprising:
      an arm coupling at least one wheel to the base; and
      at least one stop,
         wherein the at least one stop is configured so that:
            a load path for a force applied to the at least one wheel extends from the at least one wheel through the arm to the base when the at least one stop is not in engagement with the arm, and
            the load path for the force applied to the at least one wheel extends from the wheels through the arm to the at least one stop when the at least one stop is engaged with the arm.

20. The patient side cart of claim 19, wherein the cart is in the first state when the arm and the at least one stop are not in engagement with one another and the cart is in the second state when the arm and the at least one stop are engaged with one another.

21. The patient side cart of claim 19, wherein the suspension system comprises oppositely extending arm portions respectively coupling the first wheel and the second wheel to the base, the arm portions being pivotable about an axis disposed between the arm portions, the arm portions being pivotable toward and away from the base relative to a neutral position.

22. The patient side cart of claim 21, wherein the oppositely extending arm portions are configured to pivot freely about the axis at a first angular velocity through a first range of motion, and wherein the oppositely extending arm portions are configured to pivot about the axis at an angular velocity less than the first angular velocity through a second range of motion.

23. A patient side cart for a teleoperated surgical system, comprising:
    a base; and
    a manipulator portion extending from the base and configured to hold one or more surgical instruments;
    a first wheel and a second wheel;
    oppositely extending arm portions coupling the first wheel and the second wheel to the base, the arm portions being pivotable about an axis disposed between the arm portions, the arm portions being pivotable toward and away from the base relative to a neutral position; and
    first and second impact reduction mechanisms respectively disposed between the base and each oppositely extending arm portion, wherein the impact reduction mechanisms are configured to reduce an angular velocity between the wheels and the base during pivoting of the respective arm portions toward the base, and wherein the impact reduction mechanisms are spaced from the respective arm portions in the neutral position of the respective arm portions.

24. The patient side cart of claim 23, wherein the impact reduction mechanisms are spaced from the respective arm portions during a first range of motion of the respective arm portions during pivoting about the axis.

25. The patient side cart of 24, wherein during a second range of motion of the respective arm portions during pivoting about the axis, one of the impact reduction mechanisms engages one of the respective arm portions.

26. The patient side cart of claim 25, wherein during the second range of motion, a load path for force applied to the wheels extends from the wheels through the one respective arm portion and to the at least one impact reduction mechanism.

27. The patient side cart of claim 24, wherein during the first range of motion, a load path for force applied to the wheels extends from the wheels through the arm portions to the axis disposed between the arm portions.

28. The patient side cart of claim 23, wherein the impact reduction mechanisms comprise at least one compression spring.

29. The patient side cart of claim 23, wherein the first and second impact reduction mechanisms comprise a viscoelastic material.

30. The patient side cart of claim 23, further comprising first and second stops disposed to limit relative movement of the respective arm portions from the neutral position toward the base.

* * * * *